(12) United States Patent
Andersson et al.

(10) Patent No.: US 7,771,405 B2
(45) Date of Patent: Aug. 10, 2010

(54) ABSORBENT ARTICLE COMPRISING DISPOSAL FASTENING MEANS

(75) Inventors: Mikael Andersson, Göteborg (SE); Karin Stübner, Askim (SE); Ingemar Fernfors, Mölndal (SE); Anna-Gerd Doverbo, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 11/998,423

(22) Filed: Nov. 30, 2007

(65) Prior Publication Data

US 2008/0154227 A1 Jun. 26, 2008

Related U.S. Application Data

(63) Continuation of application No. PCT/SE2005/000820, filed on Jun. 1, 2005.

(51) Int. Cl.
*A61F 13/15* (2006.01)
*A61F 13/20* (2006.01)
(52) U.S. Cl. .................. 604/385.06; 604/385.02; 604/385.19
(58) Field of Classification Search .......... 604/385.01, 604/385.11, 385.13
See application file for complete search history.

(56) References Cited

U.S. PATENT DOCUMENTS

| 4,430,087 A | * | 2/1984 | Azpiri | ............... 604/385.13 |
| 5,575,784 A | | 11/1996 | Ames-Ooten et al. | |
| 6,454,748 B1 | * | 9/2002 | Ives | ............... 604/385.06 |

FOREIGN PATENT DOCUMENTS

| EP | 0 888 766 A1 | 1/1999 |
| EP | 1 269 954 A2 | 1/2003 |
| JP | 10-151153 A | 6/1998 |

* cited by examiner

*Primary Examiner*—Michele Kidwell
(74) *Attorney, Agent, or Firm*—Buchanan Ingersoll & Rooney PC (57) ABSTRACT

An absorbent article including an inner cover sheet, an outer cover sheet, and an absorbent core disposed between the inner coversheet and the outer coversheet, said article further including at least one disposal fastener, the disposal fastener having a fastening element adapted to fasten to at least a portion of the outer coversheet which allows the article to be secured in a configuration that provides a convenient disposal after the article has been used, the disposal fastener further including a pull-tab, the article further including a pocket formed by at least one of the inner cover sheet and the outer cover sheet, one end of said disposal fastener being attached to the one of the inner cover sheet and the outer cover sheet at a location within the pocket and the pull-tab protrudes from the pocket so that the disposal fastener can be pulled out from the pocket.

14 Claims, 5 Drawing Sheets

ABSORBENT ARTICLE COMPRISING DISPOSAL FASTENING MEANS

CROSS-REFERENCE TO RELATED APPLICATIONS

The present application is a continuation of international application no. PCT/SE2005/000820, filed on Jun. 1, 2005, the entire contents of which is incorporated herein by reference.

FIELD OF THE INVENTION

The present invention relates to an absorbent article such as a diaper, a pant diaper, a sanitary napkin or incontinence guard. The article comprises at least one disposal fastening means, said disposal fastening means having a fastening element adapted to fasten to at least a portion of the outer coversheet which allows the article to be secured in a configuration that provides a convenient disposal after said article has been used.

BACKGROUND TO THE INVENTION

After use, absorbent articles are usually folded or rolled up so that the soiled portion is wrapped inside for disposal. In order to prevent the soiled article unfolding and to keep the soiled portion inside, it is desired that a so-called disposal fastening means, is arranged to keep the article in the folded or rolled-up state under disposal. Usually the disposal fastening means comprises a fastening element, for example an adhesive or a mechanical fastening element, and is fixed at one end to the front or rear of the article and folded up, so that in normal use the adhesive or the mechanical fastening element is brought in an unexposed position. The strip may be unfolded so as to expose the fastening element when it is desired to use it as a disposal fastening means.

EP-A-1 121 917 discloses a pant diaper having a disposal fastening means in the form of tape strips arranged in the vicinity of the side edges of the diaper. Each tape strip comprises two portions, a first portion extending longitudinally in parallel to the side edges and a second portion extending from a predetermined region of the first portion longitudinally or transversely of the diaper. The disposal fastening means is said to be adapted to hold the diaper in its rolled up state for disposal without leakage through the waist- or leg-openings.

International patent application PCT/SE2004/002026 discloses a pant-type absorbent article comprising at least one fastening means disposed in the side joint region between the joined side edges of the article. Upon tearing the side joint region, the fastening means is exposed.

US 2003/0153891 discloses an absorbent article having a disposal fastening means, said disposal fastening means including visible indicia. These indicia make it easier to locate the disposal fastening means, and may provide instructions to a user or caregiver.

US 2002/0065500 describes a plastic hag used for disposal of diapers which is located directly on the diaper and contained within a tearable enclosure on the diaper. When disposal of the diaper is required, the enclosure is torn open, the plastic bag pulled out and the soiled diaper inserted into the plastic bag.

EP 00 623 330 discloses a shorts-type diaper provided with a tape fastener intended to fasten the used diaper when discarding. EP00732094 discloses a similar article, in which the tape fastener is elastic.

JP 2002 045401 teaches a method of fixing a folded disposal tape to the backsheet of a diaper, using an adhesion layer to keep the tape folded while the article is being worn.

Many of these previously-known disposal fastening means may be opened and even be removed by mistake by the wearer or caregiver before the article is removed for disposal. This is a particularly problem for babies, who can remove a disposal fastening means attached to their diaper, thus making it ineffective as a fastening means and a potential choking hazard for the baby. The disposal fastening means may also be opened under movements between an absorbent article and the surrounding clothing and can then stick to the clothing. If deployed accidentally, the disposal fastening means may also become soiled or damaged, and its fastening properties may be reduced.

A need exists for a disposal fastening means in which the risk of undesirable opening or removal of the disposal fastening means before the article is ready for disposal is reduced. It is also desirable that the disposal fastening means is less accessible to infants. Furthermore, the disposal fastening means should be protected from dirt and damage. The location of the disposal fastening means should be clearly noticeable to the caregiver.

SUMMARY OF THE INVENTION

The present invention aims to address the problems of the disposal fastening means of the prior art. One particular object of the present invention is to provide an absorbent article having a disposal fastening means that reduces the risk of being opened by mistake before the article is ready for disposal. It is also of particular interest to provide a disposal fastening means which is concealed and not immediately accessible, thus minimizing the risk of undesirable opening or removal.

According to the invention, an absorbent article such as a diaper, a pant diaper, a sanitary napkin or incontinence guard is provided. The absorbent article comprises an absorbent core disposed between an inner coversheet and an outer coversheet and has a longitudinal and a transverse direction. The article further comprises at least one disposal fastening means, said disposal fastening means having a fastening element adapted to fasten to at least a portion of the outer coversheet which allows the article to be secured in a configuration that provides a convenient disposal after said article has been used. The disposal fastening means also comprises a pull-tab. The invention is primarily characterized in that the disposal fastening means is located in a pocket when not in use, and that the pull-tab protrudes from said pocket, so that the disposal fastening means can be pulled out from the pocket when required.

According to one embodiment, the pocket is formed between the inner and the outer coversheet of the article. Alternatively, the outer coversheet is a laminate comprising a garment-facing layer and at least one inner layer, the pocket being formed between the inner layer and the garment-facing layer.

The pocket may be formed between the inner or the outer coversheet and a material layer which is joined separately to the coversheet. Desirably, the pocket is located on the inner surface of the inner coversheet of the article. In one embodiment, the material layer and the disposal fastening means are formed from the same piece of material.

In an embodiment of the invention, the pocket is located such that the pull-tab protrudes over an edge of the article.

Suitably, the pocket is located at the waistband of the article and arranged so that the pull-tab protrudes over the waistband of the article.

The fastening element may be a hook portion of a hook-and-loop type fastener or an adhesive tape tab. The disposal fastening means is folded within the pocket, or may comprise an elastic material such that—when not under tension—it lies hidden within the pocket but can be pulled out from the pocket under tension by pulling on the pull-tab.

Suitably, the article is a pant-type absorbent article comprising a front portion, a crotch portion and a back portion, said front and back portions being joined to each other along two opposite longitudinal side edges to define a waist-opening and a pair of leg-openings. The disposal fastening means may be located on the front or back portion of the article.

DEFINITIONS

Absorbent Article and Pant Type Absorbent Article

The term "absorbent article" refers to products that are placed against the skin of the wearer to absorb and contain body exudates, like urine, feces and menstrual fluid. The invention mainly refers to disposable absorbent articles, which means articles that are not intended to be laundered or otherwise restored or reused as absorbent articles after use.

For a diaper having fastening means in the form of adhesive tape tabs or hook-and-loop type fasteners for fastening the diaper about the waist of the wearer, this fastening means may also be used as the disposal fastening means. However, other articles, particularly pant diapers, require special disposal fastening means. The invention is therefore particularly of relevance to pant-type absorbent articles, which have a defined waist opening and a pair of leg openings and which are pulled onto the body of the wearer by inserting the legs into the leg openings and pulling the article up over the waist. Examples of such pant-type absorbent articles are pant diapers, sanitary pants and incontinence pants worn by incontinent adults. Pant-type absorbent articles usually comprise a front portion, a crotch portion and a back portion, said front and back portions being joined to each other along two opposite longitudinal side edges to define a waist-opening and a pair of leg-openings.

Inner Coversheet

The term "inner coversheet" refers to the liquid permeable material sheet forming the inner cover of the absorbent article and which in use is placed in direct contact with the skin of the wearer. The inner coversheet can comprise a nonwoven material, e.g. spunbond, meltblown, carded, hydroentangled, wet-laid etc. Suitable nonwoven materials can be composed of natural fibers, such as woodpulp or cotton fibres, manmade fibres, such as polyester, polyethylene, polypropylene, viscose etc. or from a mixture of natural and man-made fibres. The inner coversheet material may further be composed of tow fibres, which may be bonded to each other in a bonding pattern, as e.g. disclosed in EP-A-1 035 818. Further examples of inner coversheet materials are porous foams, apertured plastic films etc. The materials suited as inner coversheet materials should be soft and non-irritating to the skin and be readily penetrated by body fluid, e.g. urine or menstrual fluid. The inner coversheet may further be different in different parts of the absorbent article.

Outer Coversheet

The outer coversheet refers to the liquid impervious material forming the outer cover of the absorbent article. The outer coversheet can comprise a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The outer coversheet material may be breathable so as to allow vapour to escape from the absorbent core, while still preventing liquids from passing therethrough. Examples of breathable outer coversheet materials are porous polymeric films, nonwoven laminates of spunbond and meltblown layers and laminates of porous polymeric films and nonwoven materials. Preferably, the outer coversheet comprises nonwoven material in at least the garment-facing surface thereof.

Absorbent Core

The "absorbent core" is the absorbent structure disposed between the two coversheets of the absorbent article. The absorbent core can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as superabsorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form which is suitable for use in absorbent composites including particles, fibres, flakes, spheres, and the like.

A high absorption capacity is provided by the use of high amounts of superabsorbent material. For an absorbent core comprising a matrix of hydrophilic fibres, such as cellulosic fibres, and superabsorbent material, the proportion of superabsorbent material is preferably between 10 and 90% by weight, more preferably between 30 and 70% by weight.

It is conventional for absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed, mixed or layered structure of cellulosic fluff pulp and superabsorbent polymers. The size and absorbent capacity of the absorbent core may be varied to suit different users, such as infants or adult incontinent persons.

The absorbent core may further include an acquisition distribution layer placed on top of the primary absorbent body, which is adapted to quickly receive and temporarily store discharged liquid before it is absorbed by the primary absorbent core. Such acquisition distribution layers are well known in the art and may be composed of porous fibrous wadding or foam materials.

Disposal Fastening Means

The term "disposal fastening means" refers to a fastening means such as a strip of material which comprises a fastening element such as an adhesive tape or a mechanical fastening means in the form of hook members. The disposal fastening means is arranged such that it can fasten to the outer coversheet to keep the absorbent article in the folded or rolled up state after disposal thereof.

DESCRIPTION OF THE FIGURES

The invention will be described in further detail with reference to the figures, in which.

DETAILED DESCRIPTION OF THE INVENTION

Figure 1:
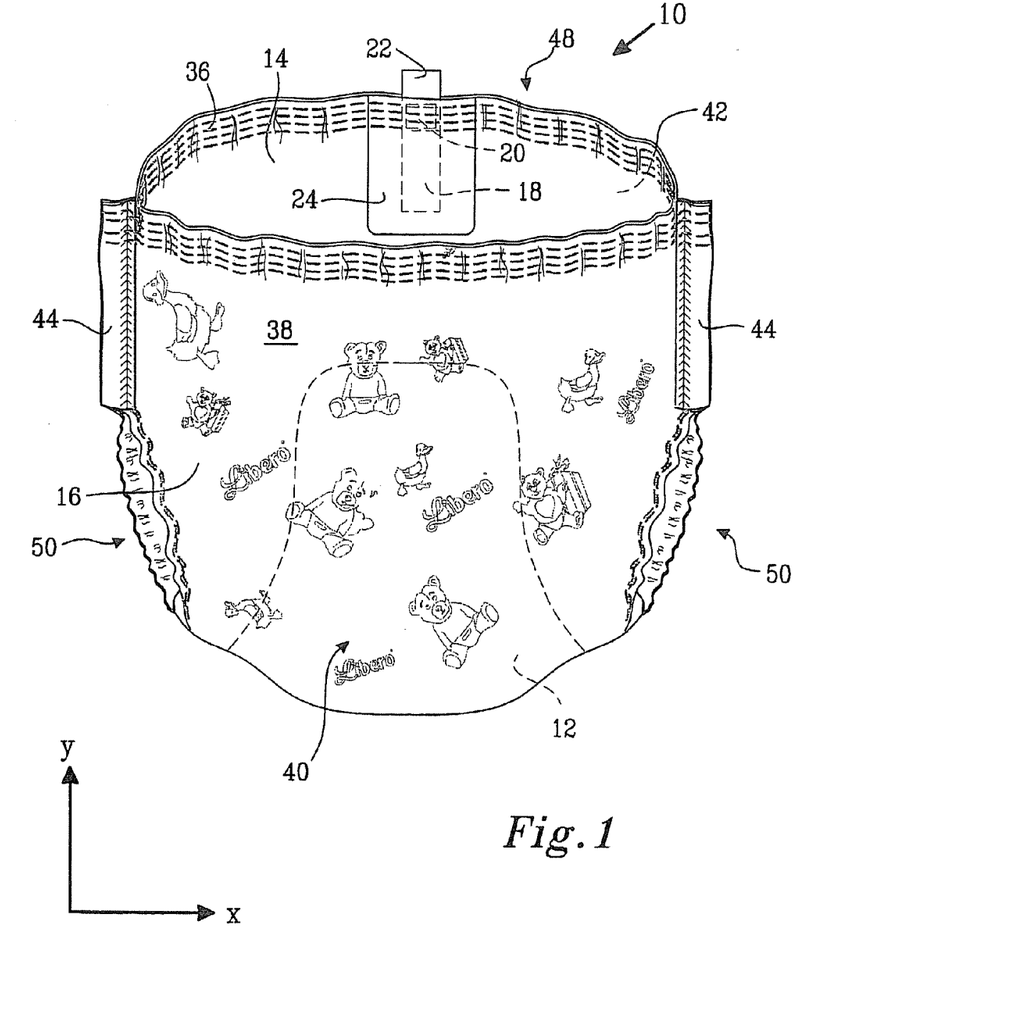
FIG. 1 shows a pant-diaper comprising disposal fastening means according to the invention.

The absorbent article 10 shown in FIG. 1 (in this case a pant diaper) comprises an absorbent core 12 which is disposed between an inner coversheet 14 and an outer coversheet 16. Pant type absorbent articles have a defined waist opening 48 and a pair of leg openings 50 and are pulled onto the body of the wearer by inserting the legs into the leg openings and pulling the article up over the waist. Examples of such pant type absorbent articles are pant diapers, sanitary pants and incontinence pants worn by incontinent adults. The pant-type absorbent article comprises a front portion 38, which is the part of the article that in use is intended to extend over the stomach and front hip area of the wearer. The article also comprises a back portion 42, which is the part of the article that in use is intended to extend over the back and the rear hip area of the wearer. The crotch portion 40 of a pant-type absorbent article is the part of the article that in use is intended to extend through the wearer's crotch area, between the legs. The front and back portions 38 and 42 may have a different material composition than the crotch portion 40.

The lateral side edges of the front 38 and back 42 portions are joined to each other to form side seams 44, wherein the article assumes a pant-like shape having the aforementioned waist opening and leg openings. The front and back portions are joined along said side seams 44, for example by adhesive, ultrasonic welding, heat sealing or the like. The front and back portions 38 and 42 can either be joined along their side edges with the inner coversheet 14 facing inwards in the side seams 44, as is shown in the drawings. Alternatively they are joined in an overlapping manner, with the inner coversheet 14 of either the front 38 or back 42 portion facing the outer coversheet 16 of the opposite portion.

The waist opening 48 and at least a part of the leg openings 50 are usually elasticized. The elastification is usually accomplished by a plurality of elastic members, such as elastic threads, which are contractably affixed between the outer coversheet 16 and the inner coversheet 14. Alternatively elastic materials, such as elastic laminates, may be used to form the front 38 or back 42 portions in those areas where elasticity is desired.

The article further comprises at least one disposal fastening means 18 as described above. The article may, for example, comprise two, three or more disposal fastening means, but in the interests of economy, only one disposal fastening means is usually present. The disposal fastening means 18 may be formed from any suitable material. Furthermore, a material layer 22 comprising nonwoven material will be well-concealed against an outer coversheet of nonwoven material, which is the material of choice for the outer coversheet. Typically, the disposal fastening means 18 is located on the front 38 or back 42 portion of the pant diaper.

Attachment of the disposal fastening means 18 to the absorbent article 10 may be via glue or welds, but should be sufficiently strong that the disposal fastening means 18 is not easily separated from the article when pulled by hand.

The disposal fastening means 18 has a fastening element 20 adapted to fasten to at least a portion of the outer coversheet 16. The fastening element 20 allows the article to be secured in a configuration that provides a convenient disposal after said article has been used. This may be a rolled-up or folded configuration. The choice of fastening element 20 depends on the nature of the outer coversheet 16—if the outer coversheet 16 is a plastic film, a suitable fastening element 20 will be an adhesive tape tab. If the outer coversheet 16 of the absorbent article 10 is a nonwoven or material layer, a suitable fastening element 20 will be a hook portion of a hook-and-loop type fastener. The skilled person will understand suitable combinations of fastening element and outer coversheet which will give the required result. The fastening element 20 is normally attached to the disposal fastening means 18 at the end of the disposal fastening means 18 which is furthest from the attachment point of the disposal fastening means to the outer coversheet 16.

The article has a longitudinal (y) and a transverse direction (x).

The disposal fastening means 18 further comprises a pull-tab 22. The pull-tab 22 may comprise a separate piece of material which is joined to the disposal fastening means 18, or which may be an integral part of the disposal fastening means 18. The pull-tab 22 should be large enough so that it can be firmly gripped by a user. Suitable materials for the pull-tab 22 are nonwoven materials or plastic films, or laminates thereof.

The disposal fastening means 18 according to the invention is located in a pocket 24 when not in use, and the pull-tab 22 protrudes from said pocket 24 so that the disposal fastening means 18 can be pulled out from the pocket 24 when required. In this way, the risk of undesirable opening or removal of the disposal fastening means 18 before the article is ready for disposal is reduced. In that the disposal fastening means 18 is located in the pocket 24, it makes it less accessible to infants. Furthermore, the pocket 24 acts to protect the disposal fastening means 18 from dirt and damage. The disposal fastening means 18 is also less likely to be twisted or otherwise undesirably folded. In that the pull-tab 22 protrudes from the pocket 24, the location of the disposal fastening means 18 is easily determined, and the disposal fastening means is readily accessible.

Figure 2:
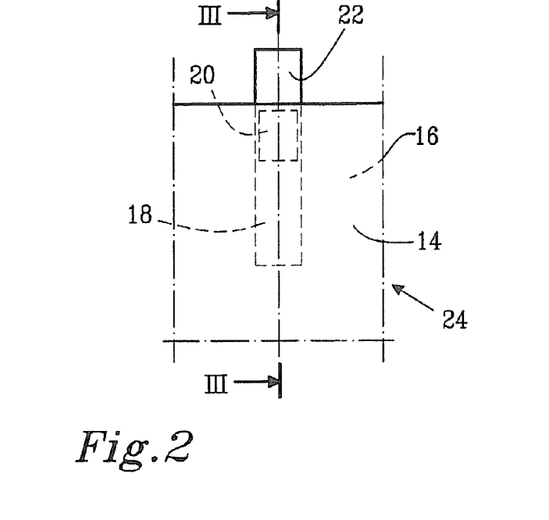
FIG. 2 shows a view of the disposal fastening means according to the invention.

FIG. 2 shows an enlargement of a fastening disposal means 18 of the present invention in which the pocket 24 is formed between the inner 14 and the outer 16 coversheet. This embodiment is readily manufactured, as the disposal fastening means 18 is included between the two coversheets during production of the article.

Figure 3:
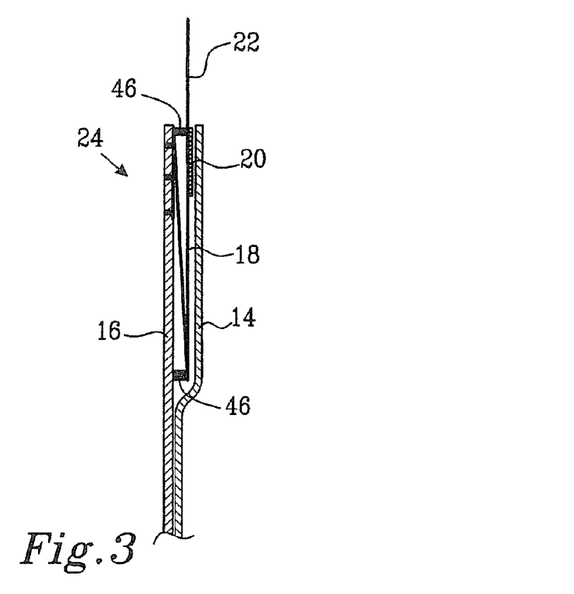
FIG. 3 is a cross-sectional view through the line III-III in FIG. 2.

FIG. 3 is a cross-sectional view along the line in FIG. 2. As can be seen in FIG. 3, the disposal fastening means 18 sits between the inner 14 and outer 16 coversheets and is therefore protected. The pull-tab 22 extends outside the pocket 24. The disposal fastening means 18 may be of a length such that it must be folded so as to fit into the pocket 24. FIG. 3 shows the disposal fastening means 18 folded in a Z-fold, although other folding forms are conceivable (e.g. C-fold). Distances between components in this figure have been exaggerated for clarity—in the actual product, the components will lie substantially in contact with one another. The disposal fastening means 18 may be held in its folded state by means of suitably-arranged glue sites or welds 46. In contrast to the glue or welds attaching the disposal fastening means 18 to the article 10, the glue or welds 46 holding the folds together will be released when the user or wearer pulls the pull-tab by hand.

Advantageously, the disposal fastening means 18 is formed from an elastic material, such that—when not under tension—the disposal fastening means 18 lies hidden within the pocket 24, but can be pulled out from the pocket 24 under tension by pulling the pull-tab 22.

Figure 4:
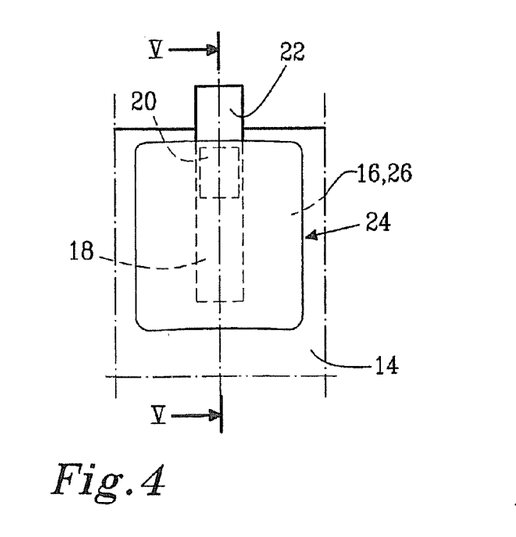
FIG. 4 is a view of an alternative embodiment of the disposal fastening means according to the invention.
Figure 5:
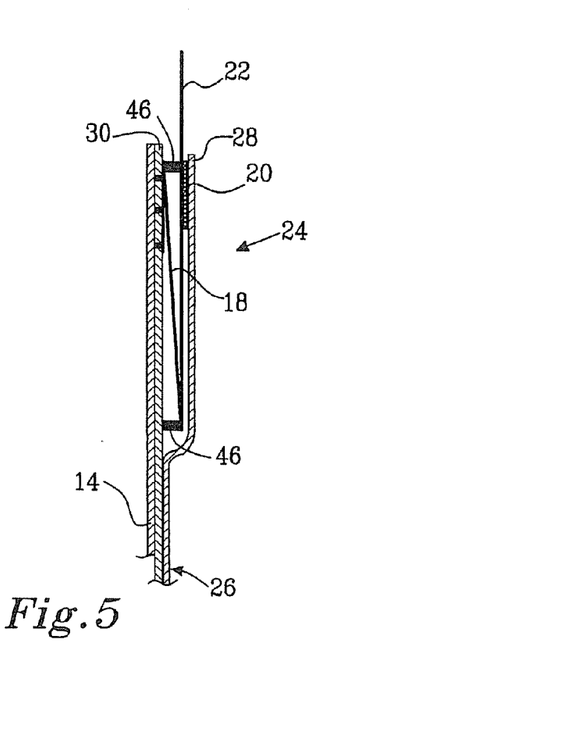
FIG. 5 is a cross-sectional view through the line V-V in FIG. 4.

FIG. 4 shows an alternative embodiment, in which the outer coversheet 16 of the article is a laminate 26. FIG. 5 is a cross-sectional view along the line V-V in FIG. 4. The laminate 26 comprises a garment-facing layer 28 and at least one inner layer 30 and the pocket 24 is formed between the inner 30 layer and the garment-facing 28 layer. The laminate 26 is suitably a laminate of a plastic film and a nonwoven material, with the nonwoven material comprising the garment-facing layer 28 of the article. As above, the disposal fastening means 18 may be folded in the pocket 24, or may be elastic. FIG. 5 shows a cross-sectional view along the line V-V in FIG. 4. Again, distances between components in these figures have been exaggerated for clarity—in the actual product, the components will lie substantially in contact with one another.

Figure 6:
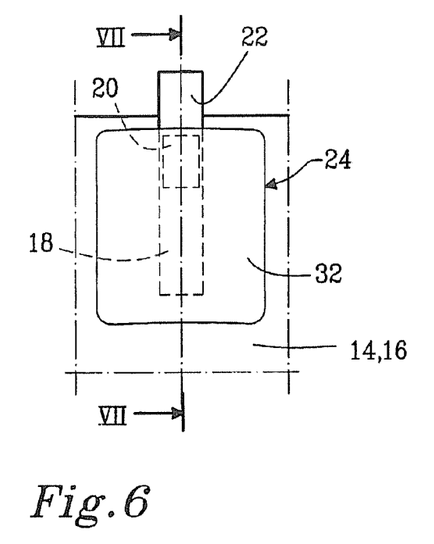
FIG. 6 is a view of an alternative embodiment of the disposal fastening means according to the invention.
Figure 7A:
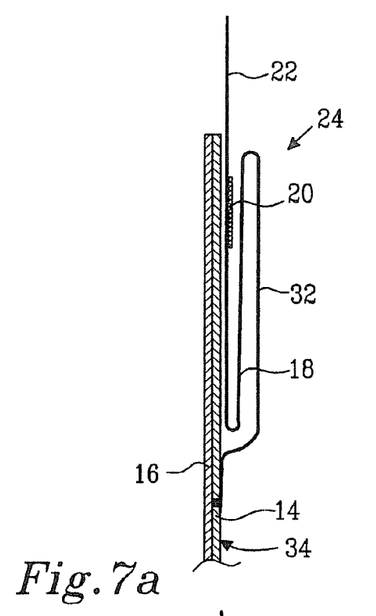
FIG. 7a is a cross-sectional view through the line VII-VII in FIG. 6.
Figure 7B:
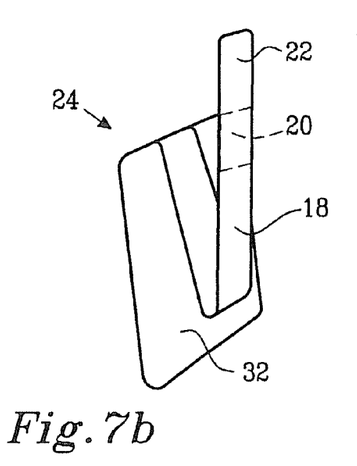
FIG. 7b illustrates the use of one piece of material to form the pocket and the disposal fastening means.
Figure 7C:
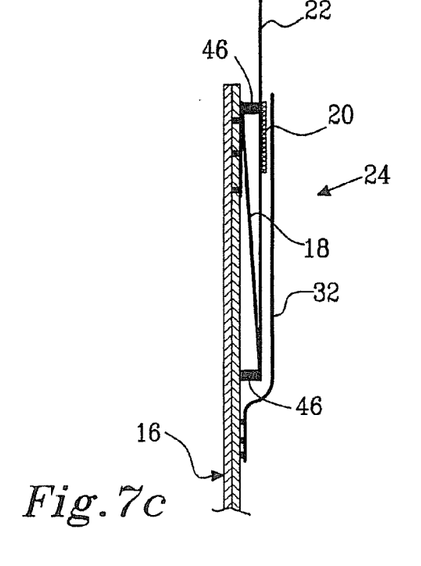
FIG. 7c is a cross-sectional view through the line VII-VII in FIG. 6 of an additional embodiment. illustrates the use of one piece of material to form the pocket and the disposal fastening means.

As an alternative to the embodiments given above, the pocket 24 is formed between the inner 14 or the outer 16 coversheet and an additional material layer 32 (see FIG. 6). This additional material layer 32 may be made from any suitable material, although nonwoven materials are particularly of interest. The pocket 24 may be located on the inner or outer surface of the article, but the pocket 24 is preferably located on the inner surface 34 of the inner coversheet 14 of the article. A cross-sectional view along the line VII-VII is shown in FIG. 7a. The additional material layer 32 and the disposal fastening means 18 may be formed from the same piece of material (see FIG. 7b). This is achieved by a piece of material which is narrower at one end and wider at the other. The thin end constitutes the disposal fastening means 18, while the wider end constitutes the additional material layer 32. During manufacture, the wider end is joined to the inner or outer coversheets 14;16 to form the pocket 24, while the thinner end of this piece of material is located in the pocket thus formed. Alternatively, the additional material layer 32 and the disposal fastening means 18 are separate entities (FIG. 7c).

To enable a carer or a user to locate and expose the disposal fastening means 18 easily, the pocket 24 is located such that the pull-tab 22 protrudes over an edge of the article 10. Preferably, this edge is the waistband 36 of the article. Most preferably, the article is a diaper or a pant diaper and the pocket 24 is located at the waistband 36 of the article and arranged so that the pull-tab 22 protrudes over the waistband 36 of the article.

As mentioned previously, the invention is most suited to pant-type absorbent articles. Such an article comprises a front portion 38, a crotch portion 40 and a back portion 42, said front and back portions 38;42 being joined to each other along two opposite longitudinal side edges to define a waist-opening and a pair of leg-openings. The disposal fastening means 18 is most conveniently, located on the front 38 or back 42 portion of the article, so that it can be readily accessed.

Figure 8A:
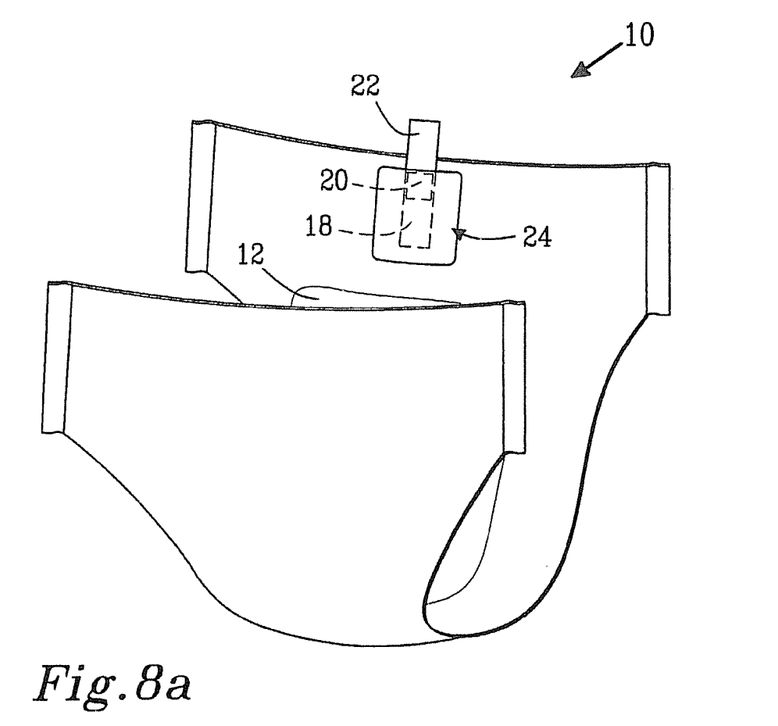
FIGS. 8a-8c illustrate how a disposal fastening means is employed.
Figure 8B:
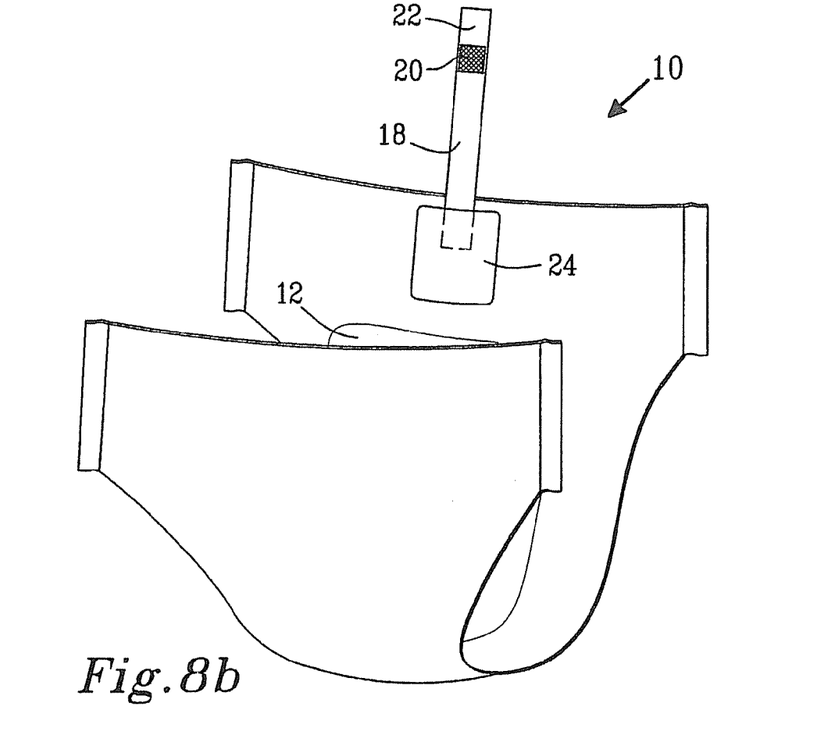
Figure 8C:
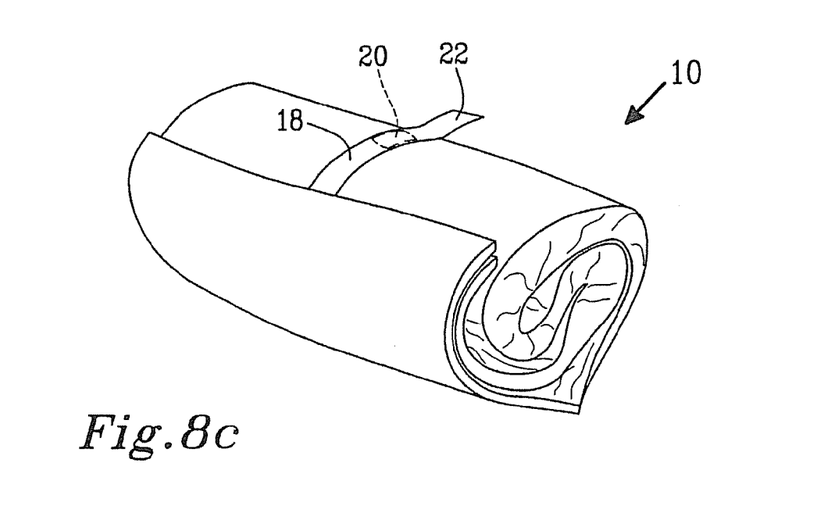

FIGS. 8a-c illustrate how the disposal fastening means 18 according to the invention is employed when disposing of a soiled diaper. One way of removing a soiled pant-type diaper is by breaking the side seams. Then, as shown in FIG. 8a, the pull-tab is pulled, thus pulling out the disposal fastening means 18 ready for use. The disposal fastening means 18 is unfolded or stretched out as necessary, as shown in FIG. 8b. Finally, the diaper is folded or rolled up into a tight package and the fastening element 20 of the disposal fastening means 18 is affixed to the outer coversheet of the diaper, so as to maintain this folded or rolled up state (FIG. 8c). Safe, hygienic disposal of the diaper is thus enabled.

The invention is not limited to the embodiments described above and shown in the drawings, but may be varied within the scope of the claims. Details from the different embodiments may of course be combined as desired, as will be evident to the person skilled in the art.

The invention claimed is:

1. An absorbent article having a longitudinal direction and a transverse direction, comprising an inner cover sheet, an outer cover sheet, and an absorbent core disposed between the inner cover sheet and the outer cover sheet, said article further comprising at least one disposal fastener, said disposal fastener having a fastening element adapted to fasten to at least a portion of the outer cover sheet which allows the article to be secured in a configuration that provides a convenient disposal after said article has been used, said disposal fastener further comprising a pull-tab, and said article further comprising a pocket formed between the inner cover sheet and the outer cover sheet, one end of said disposal fastener being directly attached to one of the inner cover sheet and the outer cover sheet at a location within the pocket, and the pull-tab protrudes from said pocket prior to use so that the disposal fastener can be pulled out from the pocket.

2. The absorbent article according to claim 1, wherein the pocket is located such that the pull-tab protrudes over an edge of the article.

3. The absorbent article according to claim 2, wherein the article is a diaper or a pant diaper and the pocket is located at the waistband of the article and arranged so that the pull-tab protrudes over the waistband of the article.

4. The absorbent article according to claim 1, wherein the fastening element is a hook portion of a hook-and-loop type fastener.

5. The absorbent article according to claim 1, wherein the fastening element is an adhesive tape tab.

6. The absorbent article according to claim 1, wherein the disposal fastener is folded within the pocket.

7. The absorbent article according to claim 1, wherein the disposal fastener comprises an elastic material such that, when not under tension, the disposal fastener lies hidden within the pocket but can be pulled out from the pocket under tension by pulling on the pull-tab.

8. The absorbent article according to claim 1, wherein the article is a pant-type absorbent article comprising a front portion, a crotch portion and a back portion, said front and back portions being joined to each other along two opposite longitudinal side edges to define a waist-opening and a pair of leg-openings.

9. The absorbent article according to claim 8, wherein the disposal fastener is located on the front or back portion of the article.

10. The absorbent article according to claim 1, wherein the article is a pant diaper, a sanitary napkin or an incontinence guard.

11. The absorbent article according to claim 1, wherein the disposal fastener comprises an elastic material.

12. An absorbent article having a longitudinal direction and a transverse direction, comprising an inner cover sheet, an outer cover sheet, and an absorbent core disposed between the inner cover sheet and the outer cover sheet, said article further comprising at least one disposal fastener, said disposal fastener having a fastening element adapted to fasten to at least a portion of the outer cover sheet which allows the article to be secured in a configuration that provides a convenient disposal after said article has been used, said disposal fastener further comprising a pull-tab, and said article further comprising a pocket formed by one of the inner cover sheet and the outer cover sheet and a material layer which is joined separately to the one of the inner cover sheet and the outer cover sheet, one end of said disposal fastener being directly attached to the one of the inner cover sheet and the outer cover sheet at a location within the pocket, and the pull-tab protrudes from said pocket prior to use so that the disposal fastener can be pulled out from the pocket, wherein the material layer and the disposal fastener are formed from one single piece of material.

13. The absorbent article according to claim 12, wherein the pocket is formed on the inner surface of the inner cover sheet.

14. An absorbent article having a longitudinal direction and a transverse direction, comprising an inner cover sheet, an outer cover sheet, and an absorbent core disposed between the inner cover sheet and the outer cover sheet, said article further comprising at least one disposal fastener, said disposal fastener having a fastening element adapted to fasten to at least a portion of the outer cover sheet which allows the article to be secured in a configuration that provides a convenient disposal after said article has been used, said disposal fastener further comprising a pull-tab, said outer cover sheet being a laminate comprising a garment-facing layer and at least one inner layer, and said article further comprising a pocket formed between the garment-facing layer and the inner layer of the outer cover sheet, one end of said disposal fastener being directly attached to the outer cover sheet at a location within the pocket, and the pull-tab protrudes from said pocket prior to use so that the disposal fastener can be pulled out from the pocket.

* * * * *